United States Patent [19]

Girijavallabhan et al.

[11] 4,435,412

[45] Mar. 6, 1984

[54] 5R,6S,8R-2-(1-METHYL-2-IMIDAZOLYLME-THYLTHIO)-6-(1-HYDROXYETHYL)-PENEM-3-CARBOXYLIC ACID

[75] Inventors: Viyyoor M. Girijavallabhan, Parsippany; Ashit K. Ganguly, Upper Montclair; Patrick A. Pinto, Mine Hill; Richard W. Versace, Ringwood, all of N.J.

[73] Assignee: Schering Corporation, Kenilworth, N.J.

[21] Appl. No.: 458,511

[22] Filed: Jan. 17, 1983

Related U.S. Application Data

[63] Continuation-in-part of Ser. No. 445,295, Nov. 29, 1982.

[51] Int. Cl.³ ............... C07D 501/36; A61K 31/425

[52] U.S. Cl. ..................... 424/270; 260/245.2 R; 260/239 A

[58] Field of Search ............... 260/245.2 R; 424/270

[56] References Cited

U.S. PATENT DOCUMENTS 4,260,618  4/1981  Christensen et al. ............. 424/270

*Primary Examiner*—Nicholas S. Rizzo
*Attorney, Agent, or Firm*—Gerald S. Rosen; Bruce M. Eisen

[57] ABSTRACT

There is disclosed the antibacterial 5R,6S,8R-2-(1-methyl-2-imidazolylmethylthio)-6-(1-hydroxyethyl)penem-3-carboxylic acid, its pharmaceutically acceptable salts and esters as well as compositions containing them and methods for their use.

15 Claims, No Drawings

5R,6S,8R-2-(1-METHYL-2-IMIDAZOLYLMETHYL-THIO)-6-(1-HYDROXYETHYL)PENEM-3-CARBOXYLIC ACID

RELATED APPLICATIONS

This application is a continuation-in-part of U.S. patent application Ser. No. 445,295 filed Nov. 29, 1982.

BACKGROUND OF THE INVENTION

This invention relates to 5R,6S,8R-2-(1-methyl-2-imidazolylmethylthio)-6-(1-hydroxyethyl)penem-3-carboxylic acid and its pharmaceutically acceptable salts and esters, which compounds possess potent anti-bacterial activity.

There is a continuing need for new antibacterial agents because continued extensive use of effective antibacterials gives rise to resistant strains of pathogens.

SUMMARY OF THE INVENTION 5R,6S,8R-2-(1-methyl-2-imidazolylmethylthio)-6-(1-hydroxyethyl)penem-3-carboxylic acid and its pharmaceutically acceptable salts and esters possess antibacterial activity against both gram-positive and gram-negative bacteria.

DETAILED DESCRIPTION

When tested in standardized microbiological assays, the compounds of this invention are active against such gram-positive organisms as *Staphylococcus epidermis* and *Bacillus subtilis*, and such gram-negative organisms as *E. coli* and Salmonella, at test levels of 0.1 to 1.0 micrograms/ml. Additionally, they show activity against organisms which product beta-lactamases, e.g., penicillinase and cephalosporinase, indicating a resistance against these enzymes. For instance, the sodium salt of 5R,6S,8R-2-(1-methyl-2-imidazolylmethylthio)-6-(1-hydroxyethyl)penem-3-carboxylic acid is active against Staphylococcus 76070105 at a test level of 0.5 microgram/ml. When tested against *E. coli* 00000589 (a beta-lactamase producing orgamism) the compound exhibits activity at 0.25 microgram/ml.

The compounds of this invention exhibit low protein binding and their metabolites have little or no unpleasant odor.

As antibacterial agents, the compounds of this invention are conventionally formulated for oral, parenteral, topical and transdermal use. Thus, this invention includes within its scope pharmaceutical compositions comprising the compounds of this invention in admixture with a pharmaceutically acceptable carrier therefor. In addition, the present invention also provides a method of treating bacterial infections in animals, particularly warm-blooded animals having a susceptible bacterial infection which comprises administering to said animal an antibacterial effective amount of a compound of this invention, or a pharmaceutical composition thereof. In the foregoing compositions, the compounds of this invention can be used as the sole active antibacterial agent or in combination with other antibacterial agents and/or enzyme inhibitors.

For oral administration, the compounds of this invention are typically formulated in the form of tablets, capsules, elixirs, or the like. For parenteral administration, they may be formulated into solutions or suspensions. Typical topical formulations are those such as lotions, creams, ointments, sprays, and mechanical delivery devices, e.g., transdermal. Parenteral administration is preferred. Typical pharmaceutically acceptable carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinyl pyrrolidone; polyvinyl alcohol; stearic acid; alkaline earth metal stearates such as magnesium stearate; vegetable oils such as peanut oil, cottonseed oil, sesame oil, olive oil and corn oil; nonionic, cationic and anionic surfactants; ethylene gylcol polymers; betacyclodextrin; fatty alcohols; hydrolyzed cereal solids; water; polyalkylene gylcols; gums; and petrolatum; as well as other non-toxic compatible fillers, binders, disintegrants and lubricants commonly used in pharmaceutical formulations. The compositions may also contain preservatives, aerosol propellants and coloring, thickening, suspending, dispensing, emulsifying, wetting, stabilizing and buffering agents.

The dosage of the compounds of this invention which is administered is dependent, in the judgement of the attending clinician, upon a variety of factors, i.e., the age and weight of the individual being treated, the mode of administration, and the type and severity of the bacterial infection being prevented or reduced. Typically, the dosage administered per day will be in the range of from about 1 to 250 mg/kg and preferably from about 5 to 20 mg/kg in divided dosages. Typically, the dosage will be administered in dosage units containing convenient amounts, for example, 125, 250 or 500 mg of active ingredient combined with a suitable physiologically acceptable carrier or diluent.

As used herein, "pharmaceutically acceptable salts" means alkali metal salts such as sodium and potassium salts; alkaline earth metal salts such as calcium, magnesium and aluminum salts; amine salts formed from a wide variety of suitable organic amines, i.e., aliphatic, cycloaliphatic, (cycloaliphatic)aliphatic or araliphatic primary, secondary or tertiary mono-, di- or polyamines, or heterocyclic bases, e.g., salts derived from triethylamine, 2-hydroxyethylamine, di-(2-hydroxyethyl)amine, tri-(2-hydroxyethyl)amine, 4-aminobenzoic acid-2-diethylaminoethyl ester, 1-ethylpiperidine, bicyclohexylamine, N,N'-dibenzylethylenediamine, pyridine, collidine, quinoline, procaine, dibenzylamine, 1-ephenamine and N-alkylpiperidine. Acid addition salts formed from mineral acids such as hydrochloric, hydrobromic, hydroiodic, phosphoric or sulfuric acids, or formed from organic carboxylic or sulfonic acids such as trifluoroacetic, para-toluene sulfonic, maleic, acetic, citric, oxalic, succinic, benzoic, tartaric, fumaric, mandelic, ascorbic and malic acids. The compounds of this invention contain a 3-carboxylic group and a basic group (the imidazole group) which form an inner salt, i.e., a Zwitterion.

"Pharmaceutically acceptable esters" means physiologically cleavable esters, i.e., metabolizable esters known in the penicillin, cephalosporin and penem arts to be easily cleaved within the body to the parent acid. Examples of such esters are indanyl, phthalidyl, methoxymethyl, glycyloxymethyl, phenylglycyloxymethyl, thienylglycyloxymethyl, acetoxymethyl and pivaloyloxymethyl.

Preparation of the foregoing salts and esters may be carried out according to conventional procedures for forming salts of beta-lactams such as penicillins, cephalosporins and penems. For example, salts of the compound can be formed, for example, by treating with metal compounds such as alkali metal salts of suitable carboxylic acids, or with ammonia or a suitable organic amine, wherein preferably stoichiometric amounts or only a small-excess of the salt-forminng agent used. Acid addition salts of the compound are obtained in the usual manner, for example, by treating with an acid or a suitable anion exchange reagent. Inner salts of the compounds of formula, i.e., a zwitterion, may be formed by neutralizing salts such as acid addition salts to the isoelectric point. The esters are preparable in a manner analogous to the preparation of the corresponding esters of penicillins and cephalosporins.

Salts may be converted in the usual manner into the free carboxy compounds.

The compounds of this invention are prepared by the processes disclosed in U.S. patent application Ser. No. 445,295, filed Nov. 29, 1982. The process disclosed therein referred to as process C is preferred for preparing the compounds of this invention. The process comprises:

(a) reacting an azetidinone of the formula

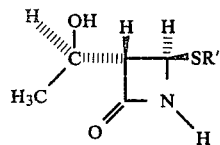

wherein R' is a sulfur protecting group selected from triphenylmethyl, 2-pyranyl, or lower alkyl carbonyl; with an α-substituted allyl acetate of formula II $$WCH_2CO_2CH_2CH=CH_2 \qquad II$$

wherein W is a leaving group; to form the intermediate of formula III

(b) treating the compound of formula III with a reactive silver, copper or mercury salt to form the compound of formula IV

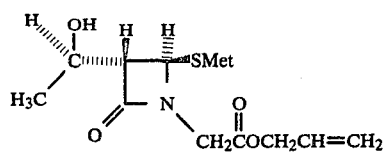

wherein Met is silver, copper or mercury.

(c) treating the compound of formula IV with a hydroxy protecting group to form the compound of formula V

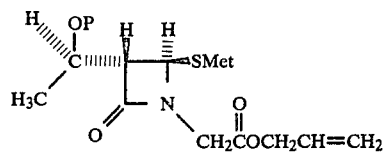

wherein P is a removable hydroxy protecting group and Met is as hereinabove defined;

(d) reacting the compound of formula V with a thiocarbonyl compound of formula VI $$S=C(-Y)_2 \qquad VI$$

wherein Y is a leaving group to form a compound of formula VII

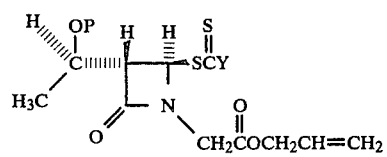

wherein Y and P are as hereinabove defined;

(e) treating compound VII with a non-nucleophilic strong base to form a compound of formula VIII(a) which is tautomeric with formula VIII(b)

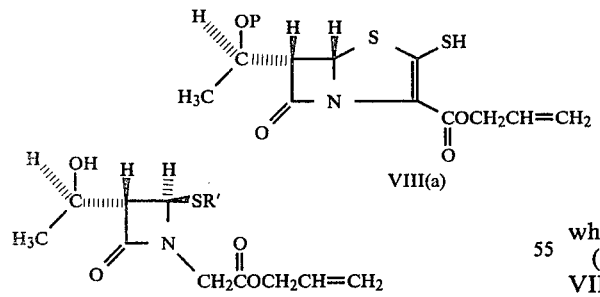

wherein P is as hereinabove defined;

(f) treating the compounds of formulas VIII(a) and VIII(b) under conditions which effect removal of the hydroxy protecting group to form the compounds of formula IX(a) and IX(b).

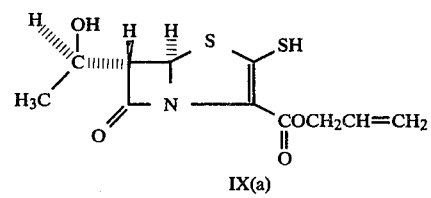
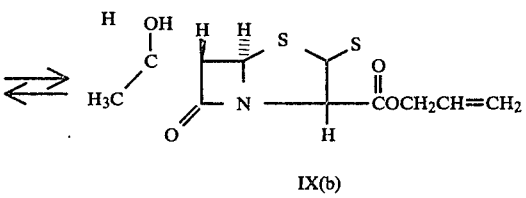

(g) reacting the compounds of formulas IX(a) and IX(b) with 1-methyl-2-chloromethylimidazole followed by removal of the allyl group to give the sodium salt of 5R,6S,8R-2-(1-methyl-2-imidazolylmethylthio)-6-(1-hydroxyethyl)penem-5-carboxylate. This salt can be converted to other salts, esters or the carboxylic acid by conventional means.

In a preferred embodiment the α-substituted allyl acetate of formula II is added to the azetidinone of formula I to form the intermediate of formula III. The intermediate of formula III is then utilized directly in steps (b), (c) and (d) which are conducted sequentially without isolation of any intermediates.

Likewise steps (e) and (f) are preferably conducted sequentially without the necessity of isolating any intermediates.

Step (a) involves the reaction of an azetidinone of formula I at 15°-30° C. in the presence of an acid acceptor with an α-substituted allyl acetate of formula II to form the compound of formula III. Preferred W leaving groups in the compound of formula II include tosyl, mesyl, chloro, bromo, iodo, and trifluoromethansulfonyl. Particularly preferred W leaving groups are iodo and bromo.

Where the solvent utilized is also an acid acceptor, for instance, pyridine, no additional reagent is utilized. Alternatively, an organic solvent such as acetonitrile may be employed. In these cases, a separate acid acceptor, organic or inorganic must be added to the system. Preferably, the reaction is conducted in acetonitrile employing cesium carbonate or tetra alkyl ammonium hydroxide as the acid acceptor.

Step (b) involves the conversion of the compound of formula III to the corresponding salt of formula IV. Step (c) involves the protection of the 6-hydroxy substituent to form the compound of formula V with the preferred protecting group being trimethylsilyl whereas step (d) is that wherein the metal salt of formula V is then converted to a compound of formula VII by addition of a thiocarbonyl reagent of formula VI wherein the Y leaving group is typically chloro, bromo, iodo or imidazolyl. For the purposes of this process, 1,1'-thiocarbonyldiimidazole is the preferred thiocarbonyl reagent due to its crystalline nature and ease of use.

In Step (b) typically, a polar solvent such as methanol, ethanol, dimethylformamide (DMF), tetrahydrofuran or water is utilized. Metal salts, e.g. those of silver, mercury or copper can be utilized in this step and may be and reactive salt of the metal in which the anion does not interfere in the reaction. Silver salts are preferred and include organic and inorganic salts such as silver nitrate, silver fluoborate and silver acetate, and the like with silver nitrate being most preferred. Typical suitable copper salts are those such as copper (II) acetate and copper (II) nitrate. Typical suitable mercury salts are those such as mercuric acetate. Lead salts may also be utilized although the reaction will be much slower. Silver salts are most preferred due to their ease of recovery and relative nontoxicity. The use of an acid acceptor, e.g., pyridine or triethylamine, facilitates the reaction of this step. The reaction preferably takes place under an inert atmosphere with a nitrogen atmosphere preferred.

Step (c) involves the protection of the 6-hydroxy substituent. Hydroxy protecting groups are well known in the beta lactam art. A particularly preferred reagent for this step is bis trimethyl silylacetamide which readily forms the trimethylsilyl protecting group at the 6-hydroxy moiety. Preferably step (c) is conducted directly upon the completion of step (b) without isolation of the metal salt intermediate of formula IV. Thus the inert solvent utilized, e.g. DMF, may be the same as the one used in step (b). Solvents such as chloroform, methylene chloride and the like may also be employed in step (c). Temperatures for the reaction of step (c) range from 0° C. to 30° C.

Step (d) is wherein the metal salt of formula V is converted to the thiocarbonyl compound of formula VII by reaction of the compound of formula V with the thiocarbonyl reagent of formula VI. Typically, this step (d) is conducted directly upon the completion of step (c) without isolation of the metal salt intermediate of formula V. Thus, the solvent utilized may be the same as the one used in step (c). Temperatures for the reaction of step (d) range from about 10° C.-45° C., with room temperature (about 25° C.) being generally preferred.

Step (e) involes the cyclization of the compound of formula VII into the thione of formulas VIII(a) and VIII(b). The reaction is typically conducted in an anhydrous inert organic solvent such as tetrahydrofuran and the like. An essentially equimolar amount of a strong base such as lithium diisopropyl amide (LDA), lithium di(trimethylsilyl) amine and the like is added to the system to effect cyclization. Typically, the reaction is conducted at from −50° to −100° C. and preferably at −70° C. and is generally complete from within 5 minutes to 24 hours.

Step (f) involves the removal of the 6-hydroxy protecting group in the compound of formulas VIII(a) and VIII(b) to form the compound of formulas IX(a) and IX(b).

Methods for the removal of this group are well known in the β-lactam art. Preferably, when the 6-hydroxy protecting group is trimethylsilyl, addition of a mild aqueous acid solution, such as acetic acid, to the same solution as is employed in step (e) effects removal.

The term "removable hydroxy protecting group" as used herein means any such group conventionally used for this purpose, with the only requirement being compatibility with the hydroxy substituent on the penems and removability utilizing elemental zinc or any other conventional agent for this purpose which will not adversely affect the penem structure. For the purpose of this invention, preferred hydroxy protecting groups include trichloroethoxycarbonyl, dimethyltributylsilyl, trimethylsilyloxycarbonyl and trimethylsilyl.

Step (g) is wherein the compound of formulas IX(a) and IX(b) are reacted with 1-methyl-2-chloromethylimidazole. The reaction is conducted in an inert atmosphere, such as nitrogen, in an organic solvent such as tetrahydrofuran (THF) at cold temperatures, e.g. 0° C., the reaction is completed within 1 to 3 hours to yield 5R,6S,8R, allyl-2-(1-methyl-2-imidazolylmethylthio)-6-(1-hydroxymethyl)penem-3-carboxylate.

Removal of the allyl group is effected by the addition of the above allyl ester to a solution containing palladium (zero) and an alkali alkylcarboxylate, or aqueous carbonate. This is described by McCombie in U.S. Pat. No. 4,314,942 which is incorporated herein by reference. Under these conditions, the removal of the allyl group and formation of the alkali salt of the compound occurs.

The following examples illustrate the preparation of the compound and compositions of this invention.

EXAMPLE 1

PREPARATION OF ALLYL
(5R,6S,8R)-2-THIOL-6-(1-HYDROXYETHYL)-
PENEM-3-CAROXYLATE AND ALLYL
(5R,6S,8R)-2-THIOCARBONYL-6-(1-HYDROXYE-
THYL)PENEM-3-CARBOXYLATE (A) Preparation of
(3S,4R)-1-(allyloxycarbonylmethyl)-3-(1-hydroxye-
thyl)-4-(triphenylmethylthio)azetidin-2-one Add 3 gm of (3S,4R)-3-(1-hydroxyethyl)-4-(triphenylmethylthio)azetidin-2-one to 10 ml of acetonitrile containing 0.286 gm of cesium carbonate. Add 0.2 gm of α-iodo allyl acetate to the system. Stir the system at room temperature for 16 hours. Dilute with ether (50 ml), filter and wash the ether layer with 1% aqueous phosphoric acid, followed by water. After drying over sodium sulfate remove solvent to give a foamy solid.

NMR: $\delta = 8.4$, 1H, s; 7.65, 1H, d(J=1 Hz); 7.05, 1H (dJ=1 Hz); 5.95, 1H, d (J=2 Hz); 5.8, 1H, m; 5.45-5.1, 2H, m; 4.3, 1H, m; 4.1, 2H, Q(J=16 Hz); 3.5, d d (J=2,6); 1.35; 3H, d (J=6 Hz).

(B) Preparation of Silver
(3S,4S)-3-(1-hydroxyethyl)-1-allylcarbonylmethylazeti-
din-2-one-4-thiolate To a 50 ml flask equipped with a nitrogen atmosphere add 10 ml of methanol and 460 mg of (3S,4R)-1-(allyloxycarbonylmethyl)-3-(1-hydroxyethyl)-4-triphenylmethylthio)azetidin-2-one. To this system add 160 mg silver nitrate and 0.15 ml of pyridine. Stir the system at 20° C. for 1 hour. Stop the reaction and remove the methanol by stripping to give the title compound.

(C) Preparation of Silver
(3R,4R)-3-(1-trimethylsilyloxy)ethyl)-1-allyloxycar-
bonylmethylazetidin-2-one-4-thiolate Add the entire amount of silver (3S,4R)-3-(1-hydroxyethyl)-1-allyloxycarbonylmethylazetidin-2-one-4-thiolate produced in step (B) above to 25 ml of methylene chloride. To this system add 1.1 ml of bis trimethyl silylacetamide. Stir the system at room temperature for 15 minutes to give the title compound.

(D) Preparation of
(3S,4R)-1-(allyloxycarbonylmethyl)-3-(1-trimethyl-
silyloxyethyl)-4-(1-imidazolylthiocarbonylthio)-azeti-
din-2-one After completion of step (C) above and to the same solution add 350 mg of thiocarbonyldiimidazole. Stir the system at room temperature for 3 hours. Filter the solution and wash the precipitate with methylene chloride. Collect the filtrate and remove the methylene chloride by stripping. Chromatograph the residue on silica gel eluting with 20% ethyl acetate/methylene chloride to yield 335 mg of the title compound.

(E) Preparation of (5R,6S,8R)
allyl-2-thiol-6-(1-trimethylsilyloxyethyl)penem-3-car-
boxylate and (5R,6S,8R)
allyl-2-thiocarbonyl-6-(1-trimethylsilyloxyethyl)penam Add 170 mg of (3S,4R)-1-(allyloxycarbonylmethyl)-3-(1-trimethylsilyloxyethyl)-4-(1-imidazolylthiocarbonylthio)azetidin-2-one to 40 ml of anhydrous tetrahydrofuran under a nitrogen atmosphere. Cool the system to −78° C. and then add 0.6 ml of 1 M lithium di-(trimethylsilyl) amine in hexane dropwise to the system. Stir the system at −78° C. for 5 minutes. Add 0.2 ml of acetic acid to the system. Dilute the system to 200 ml with methylene chloride. Wash the organic solution with water, aqueous sodium bicarbonate solution and again with water. Purify the product by chromatography by rapidly eluting the sample through silica gel with 5% ethyl acetate/methylene chloride to afford 125 mg of the desired products and the desilylated products.

(F) Preparation of (5R,6S,8R)
Allyl-2-thiol-6-(1-hydroxyethyl)penem-3-carboxylate
and (5R,6S,8R)
Allyl-2-thiocarbonyl-6-(1-hydroxyethyl)penem To a 25 ml flask add the entire mixture produced in step (E) along with 5 ml of tetrahydrofuran, 1 ml of water and 1 ml of acetic acid. Stir the system at room temperature for 2 hours. Add ethyl acetate to the solution and wash the organic phase with sodium bicarbonate solution, water and then brine. Dry the organic phase over anhydrous sodium sulfate, filter and remove the solvent by stripping to give the title compound.

EXAMPLE 2

5R,6S,8R
ALLYL-2-(1-METHYL-2-IMIDAZOLYMETHYL-
THIO)-6-(1-HYDROXYETHYL)PENEM-3-CAR-
BOXYLATE

Charge to a 250 ml flask under nitrogen 1.38 gram of the thione of Example 1, 50 ml of tetrahydrofuran (THF) and 1.2 gram of 1-methyl-2-chloromethylimidazole. Cool to 0° C. Add dropwise over 3 minutes 1.15 gram of NaHCO$_3$ as a 10% aqueous solution. Stir for about 45 minutes and let stand for one hour at 0° C. Remove the THF solvent and recover the title product on a silica column.

NMR-(CDCl$_3$)$\delta$=6.95, 1H, s; 6.86, 1H, s; 5.9, 1H, m; 5.73, 1H, d; 5.32, 2H, m; 4.7, 2H, m; 4.3, 2H, s; 4.2, 1H, m; 3.7, 1H, dd (J=1.5, 6 Hz); 3.68, 3H, s; 1.3, 3H, d (J=6 Hz).

EXAMPLE 3

1-METHYL-2-CHLOROMETHYL-IMIDAZOLE

Charge 10 grams of 1-methyl imidazole and 100 ml of a 37% aqueous formaldehyde solution to a 150 ml Parr bomb and heat to 125° C. in an oil bath. Remove the water and evaporate the residue to a gel. Extract the gel in solution with methanol. Remove the methanol. Isolate from a coarse silica column, the product, 1-methyl-2-hydroxymethyl-imidazole, and crystallize from CCl$_4$. Mix 4.4 gram of 1-methyl-2-hydroxymethyl-imidazole with 5.7 ml SOCl$_2$ in 50 ml CHCl$_3$ in a reaction flask. Stir for 18 hours and remove the solvent and excess SOCl$_2$ under vacuum. Evaporate to dryness to recover the product, 1-methyl-2-chloromethyl-imidazole.

EXAMPLE 4

5R,6S,8R,-2-(1-METHYL-2-IMIDAZOLYLME-
THYLTHIO)-6-(1-HYDROXYETHYL)PENEM-3-
CARBOXYLIC ACID

Dissolve 1.05 grams of the product of Example 2 in 40 ml of the ethylacetate. React at room temperature with about 200 mg Pd° reagent, 200 mg triphenyl phosphine and 1.5 ml hexanoic acid. Extract the resulting title compound with water. Increase the yield by dissolving unreacted starting material in 15 ml CH$_2$CL$_2$, 1 ml hexanoic acid, 0.3 ml pyridine, 1.50 mg triphenyl phosphine and about 100 mg Pd° for ½ hour. Extract the title compound with water and combine with the previous extract—the product has NMR-(D$_2$O)δ=7.3, 1H, s; 7.27, 1H, s; 5.6, 1H, d(J=1.6 Hz.); 4.4, 2H, m; 4.2, 1H, m; 3.85, 1H, dd(J=1.5, 6 Hz.); 3.81, 3H, s; 1.24, 3H, d(J=6 Hz).

In the following examples, the Active Ingredient is 5R,6S,8R-2-(1-methyl-2-imidazolylmethylthio)-6-(1-hydroxyethyl)penem-3-carboxylic acid and an equivalent amount of any of its pharmaceutically acceptable salts and esters.

EXAMPLE 5

| No. | Ingredient | Capsules mg/capsule | mg/capsule |
|---|---|---|---|
| 1. | Active ingredient | 250 | 500 |
| 2. | Lactose USP | 100 | 50 |
| 3. | Corn Starch, Food Grade | 50 | 43.5 |
| 4. | Microcrystalline Cellulose NF | 95 | 50 |
| 5. | Magnesium Stearate NF | 5 | 6.5 |
|   | Total | 500 | 650 |

Method of Manufacture

Mix Items Nos. 1, 2, 3 and 4 in a suitable mixer for 10–15 minutes. Add Item No. 5 and mix for 1–3 minutes. Fill the mixture into suitable two-piece hard gelatin capsules using encapsulating machine.

EXAMPLE 6

| No. | Ingredient | Tablets mg/capsule | mg/capsule |
|---|---|---|---|
| 1. | Active ingredient | 250 | 500 |
| 2. | Lactose USP | 57 | 114 |
| 3. | Corn Starch, Food Grade, as a 10% paste in Purified Water | 20 | 40 |
| 4. | Corn Starch, Food Grade | 18 | 39 |
| 5. | Magnesium Stearate NF | 5 | 7 |
|   | Total | 350 | 700 |

Method of Manufacture

Mix Items Nos. 1 and 2 in a suitable mixer for 10–15 minutes. Granulate the mixture with Item No. 3. Paste wet granulation through a course screen (e.g., ¼″) if needed, and dry the wet granules. Mill the dried granules. Combine Item No. 4 and the dried granules and mix for 10–15 minutes. Add Item No. 5 and mix for 1–3 minutes. Compress the mixture to appropriate size and weight on a suitable tablet machine.

EXAMPLE 7

| Injectable Powder: (per vial) | | |
|---|---|---|
|   | g/vial | g/vial |
| Active Ingredient | 0.5 | 1.0 |

Add sterile water for injection or bacteriostatic water for injection for reconstitution.

EXAMPLE 8

| Ingredient | Injectable Solution mg/ml | mg/ml |
|---|---|---|
| Active Ingredient | 100 | 500 |
| Methylparaben | 1.8 | 1.8 |
| Propylparaben | 0.2 | 0.2 |
| Sodium Bisulfite | 3.2 | 3.2 |
| Disodium Edetate | 0.1 | 0.1 |
| Sodium Sulfate | 2.6 | 2.6 |
| Water for Injection q.s. ad | 1.0 ml | 1.0 ml |

Method of Manufacture

1. Dissolve parabens in a portion (85% of the final volume) of the water for injection at 65°–70° C.
2. Cool to 25°–35° C. Charge and dissolve the sodium bisulfite, disodium edetate and sodium sulfate.
3. Charge and dissolve the active ingredient.
4. Bring the solution to final volume by adding water for injection.
5. Filter the solution through 0.22 membrane and fill into appropriate containers.
6. Terminally sterilize the units by autoclaving.

EXAMPLE 9

| Injectable Powder: (per vial) | |
|---|---|
|   | g/vial |
| Active Ingredient | 1.0 |
| Sodium Citrate | 1.05 | pH is adjusted to 6.2 using 0.1 N citric acid solution.

Add sterile water for injection or bacteriostatic water for injection for reconstitution.

We claim:

1. 5R,6S,8R-2-(1-methyl-2-imidazolylmethylthio)-6-(1-hydroxyethyl)penem-3-carboxylic acid and the pharmaceutically acceptable salts and esters thereof.

2. The compound of claim 1 wherein the pharmaceutically acceptable salt is an alkali metal salt.

3. The compound of claim 1 wherein the pharmaceutically acceptable salt is an alkaline earth metal salt.

4. The compound of claim 1 wherein the pharmaceutically acceptable salt is an amine salt.

5. The compound of claim 1 wherein the pharmaceutically acceptable salt is an acid addition salt.

6. The compound of claim 1 wherein the pharmaceutically acceptable esters are metabolizable esters.

7. The compound of claim 2 wherein the alkali matal is sodium.

8. An antibacterially effective pharmaceutical composition comprising an antibacterial effective amount of a compound of claim 1 in admixture with a pharmaceutically acceptable carrier therefor.

9. A composition according to claim 8 adapted for oral administration.

10. A composition according to claim 8 adapted for parenteral administration.

11. A composition according to claim 8 adapted for topical administration.

12. A method of treating or preventing susceptible bacterial infections which comprises administering to a host in need of such treatment or prevention a compound of claim 1 or a pharmaceutical composition thereof in an amount sufficient to treat or prevent such infection.

13. A method according to claim 12 wherein the route of administration is oral.

14. A method according to claim 12 wherein the route of administration is parenteral.

15. A method according to claim 12 wherein the route of administration is topical.

* * * * *